(12) United States Patent
Kamionka et al.

(10) Patent No.: US 10,576,467 B2
(45) Date of Patent: Mar. 3, 2020

(54) MATERIALS AND METHODS FOR THE SELECTIVE RECOVERY OF MULTIVALENT PRODUCTS

(71) Applicant: INVISTA NORTH AMERICA S.A.R.L., Wilmington, DE (US)

(72) Inventors: Mariusz Kamionka, Redcar (GB); Alex Conradie, Eaglescliffe (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 15/564,882

(22) PCT Filed: Apr. 8, 2016

(86) PCT No.: PCT/US2016/026754
§ 371 (c)(1),
(2) Date: Oct. 6, 2017

(87) PCT Pub. No.: WO2016/164798
PCT Pub. Date: Oct. 13, 2016

(65) Prior Publication Data
US 2018/0111892 A1     Apr. 26, 2018

Related U.S. Application Data

(60) Provisional application No. 62/144,884, filed on Apr. 8, 2015.

(51) Int. Cl.
C02F 1/20     (2006.01)
C02F 1/42     (2006.01)
(Continued)

(52) U.S. Cl.
CPC .............. B01J 49/05 (2017.01); B01J 39/05 (2017.01); B01J 39/18 (2013.01); B01J 47/014 (2017.01);
(Continued)

(58) Field of Classification Search
CPC . B01J 39/18; B01J 47/014; B01J 47/11; B01J 49/05; C02F 1/42; C02F 209/86;
(Continued)

(56) References Cited

U.S. PATENT DOCUMENTS 3,393,233 A     7/1968  Richter
4,263,145 A *   4/1981  Wirth, Jr. ............... B01J 47/04
                                                            210/675

(Continued)

FOREIGN PATENT DOCUMENTS

WO     1990/08730 A1     8/1990
WO     2016/164798 A1   10/2016

OTHER PUBLICATIONS

International Preliminary Report on Patentability issued in International Application No. PCT/US2016/026754 dated Oct. 19, 2017, 10 pages.

(Continued)

Primary Examiner — Pancham Bakshi
Assistant Examiner — Mark R Luderer
(74) Attorney, Agent, or Firm — INVISTA North America S.a.r.l.

(57) ABSTRACT

Described herein are processes and apparatus for the high purity and high concentration recovery of multivalent products via continuous ion exchange from aqueous solutions for further down-stream purification.

12 Claims, 5 Drawing Sheets

(51) Int. Cl.
*B01J 39/05* (2017.01)
*B01J 39/18* (2017.01)
*B01J 47/11* (2017.01)
*B01J 49/05* (2017.01)
*B01J 49/60* (2017.01)
*B01J 47/014* (2017.01)
*B01J 47/016* (2017.01)
*C02F 101/34* (2006.01)
*C02F 101/38* (2006.01)
*C07C 209/86* (2006.01)

(52) U.S. Cl.
CPC ............. *B01J 47/016* (2017.01); *B01J 47/11* (2017.01); *B01J 49/60* (2017.01); *C02F 1/42* (2013.01); *C07C 209/86* (2013.01); *C02F 1/20* (2013.01); *C02F 2101/34* (2013.01); *C02F 2101/38* (2013.01); *C02F 2303/16* (2013.01)

(58) Field of Classification Search
CPC .... C02F 1/20; C02F 2101/34; C02F 2101/38; C02F 2303/16
See application file for complete search history.

(56) References Cited

U.S. PATENT DOCUMENTS

| | | |
|---|---|---|
| 6,284,904 B1 | 9/2001 | Ponnampalam |
| 9,878,321 B2 * | 1/2018 | Kamionka ............... B01J 39/18 |
| 2012/0289742 A1 * | 11/2012 | Gerberding ............. C07C 51/43 |
| | | 562/580 |
| 2016/0296926 A1 | 10/2016 | Karnionka et al. |

OTHER PUBLICATIONS

International Search Report and Written Opinion issued in International Application No. PCT/US2016/026754 dated Jun. 17, 2016, 11 pages.
U.S. Non-Final Office Action issued in copending U.S. Appl. No. 15/094,930 filed on Apr. 8, 2016 dated Jun. 2, 2017, 12 pages.
U.S. Notice of Allowance mailed in copending U.S. Appl. No. 15/094,930 filed on Apr. 8, 2016 dated Sep. 21, 2017, 7 pages.

* cited by examiner

FIGURE 3

| | Unit | Hexamethylene-diamine | Lysine | Glutamate | 3-hydroxybutyrate | Pyruvate |
|---|---|---|---|---|---|---|
| Feed purity | [%] (w/w) | 77.4 | 3.0 | 6.4 | 4.4 | 8.8 |
| Adsorption loading | [g/(L resin)] | 103.1 | 2.4* | 1.2 | -1.0* | 0 |
| Post monovalent adsorption loading | [g/(L resin)] | 139.8 | 0.7 | 0.5 | | |
| Concentrating fold increase | [-] | 1.36 | 0.3 | | | |
| Elution purity | [%] (w/w) | 99.2 | 0.5 | 0.3 | | |

*Mass balance closure across the unit operation not within ±10 [%].

FIGURE 4

| | Unit | Hexamethylene-diamine | Lysine | Glutamate | 3-hydroxybutyrate | Pyruvate |
|---|---|---|---|---|---|---|
| Feed purity | [%] (w/w) | 88.1 | 1.6 | 2.4 | 3.4 | 4.6 |
| Adsorption loading | [g/(L resin)] | 155.6 | 1.2 | 0.1 | -2.7* | -0.4 |
| Post monovalent adsorption loading | [g/(L resin)] | 214.6 | 0.7 | | | |
| Concentrating fold increase | [-] | 1.38 | 0.6 | | | |
| Elution purity | [%] (w/w) | 99.6 | 0.4 | | | |

*Mass balance closure across the unit operation not within ±10 [%].

MATERIALS AND METHODS FOR THE SELECTIVE RECOVERY OF MULTIVALENT PRODUCTS

This application is the U.S. National Stage of International Application No. PCT/US2016/026754 filed Apr. 8, 2016, which claims priority to U.S. provisional application No. 62/144,884, filed on Apr. 8, 2015, each of which is herein incorporated by reference in its entirety.

TECHNICAL FIELD

The present disclosure relates to materials and methods for the selective recovery of one or more multivalent product. The present disclosure relates to methods for the selective recovery of a multivalent product from an aqueous solution using, for example, continuous ion exchange. In combination with an ammonia/ammonium carbonate stripper, the materials and methods of the present disclosure produce a high purity, high concentration intermediate product stream for further purification, lowering the cost of the overall downstream processing.

SUMMARY

Multivalent products, i.e. molecules that exhibit more than one valence, require high concentration recovery from aqueous solutions at high purity for further purification. For example, the amino acid L-arginine is largely divalent at pH ~1 and largely monovalent at p~ 4. L-arginine may be produced via fermentation into an aqueous medium, which includes inorganic ionic species and organic by-products, e.g. monovalent amino acids, as competitive species in adsorption processes such as ion exchange. Such monovalent by-products compete for adsorption sites at a pH ~4, resulting in a. lower purity, high concentration, intermediate stream for purification. Recovery of divalent L-arginine at pH ~1 allows rejection of monovalent by-products from the ion exchange resin producing a high purity product, but reduces the concentration of the intermediate stream for purification.

Many other multivalent products produced into an aqueous medium require high purity and high concentration recovery prior to further economical purification. Such multivalent products include, but are not limited to, (1) dicarboxylic acids such as succinic acid, glutaric acid, adipic acid, pimelic acid and (2) diamines such as putrescine, cadaverine, hexamethylenediamine, heptamethylenediamine. Accordingly, against this background, it is clear that there is a need for methods underpinning the economic recovery of such multivalent products from aqueous solutions.

Recovery methods for purification of multivalent products can be implemented by a variety of different separation techniques. A non-limiting example includes optimizing the binding capacity of the charged compound via ion exchange. Ion exchange may involve at least one stage of adsorption, elution, and regeneration and in some applications, may include several regeneration and washing phases. "Batch mode" involves applying a mixture to a single column and applying various eluents in succession to improve adsorption of the target compound to the ion exchange resin. After the adsorption step, the ion exchange resin can be regenerated with the appropriate eluent to repeat the process in a cyclical manner that does not attain steady state. Batch mode systems may be simple to use but can be impractical for large-scale industrial processes. Continuous ion exchange may allow for simultaneous adsorption and regeneration steps and thus, be more efficient since there is an automated, continuous staging of the recovery process that attains steady state operation. And, given the trade-off between producing a high purity product at high concentration without significant recovery loss, continuous ion exchange offers an alternative approach achieving both aims for multivalent products.

Accordingly, the present disclosure relates to materials and methods of recovering multivalent products at high purity and high concentration from an aqueous solution via continuous ion exchange using either cationic or anionic ion exchange adsorbents.

In at least one embodiment, the present disclosure provides for an apparatus comprising a continuous ion exchange carousel comprising a number of columns grouped into zones, for example, (1) a Dilute Adsorption Zone, (2) an Adsorption Zone, (3) an Adsorption Wash Zone, (4) a Back-Wash Zone, (5) a Monovalent Strip Zone, (6) a Monovalent Adsorption Zone, (7) an Elution Zone and (8) an Elution Wash Zone.

In one aspect, the disclosed methods provide for the recovery of a multivalent product from an aqueous solution, feeding an unclarified or clarified solution to the continuous ion exchange unit operation, principally adsorbing the multivalent product as the divalent specie in the Adsorption Zone and Dilute Adsorption Zone.

In another aspect, the disclosed methods selectively desorb monovalent by-products from the adsorbent and modifies the valence of the multivalent product from divalent to monovalent in the Monovalent Strip Zone.

In another aspect, the continuous ion exchange unit operation provides for concentrating re-adsorbing of the principally monovalent specie of the multivalent product on the ion exchange adsorbent in the Monovalent Adsorption Zone, fed from an ammonia/ammonium carbonate steam stripper unit operation.

In another aspect, the Monovalent Strip Zone and the Monovalent Adsorption Zone are combined; where the principally zero valence specie of the multivalent product, fed from an ammonia/ammonium carbonate stripper unit operation, both selectively desorbs monovalent by-products from the adsorbent and modifies the valence of the multivalent product from the divalent to the monovalent providing for concentrating re-adsorption onto the adsorbent.

In one aspect, the methods provide for the recovery of the multivalent product via elution from the ion exchange adsorbent using an ammonia, ammonium bicarbonate or ammonium carbonate solution as an eluent. Free ammonia and carbon dioxide are stripped from the eluate using a steam stripper.

In yet another aspect, the present disclosure relates to a bio-derived product, bio-based product or fermentation-derived product, wherein said product is obtained from process disclosed herein, and comprises:

i. a composition comprising at least one bio-derived, bio-based or fermentation-derived compound according to any one of processes disclosed herein, or any one of FIGS. 1-4 or any combination thereof.

ii. a bio-derived, bio-based or fermentation-derived polymer comprising the bio-derived, bio-based or fermentation-derived composition or compound of i., or any combination thereof, iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof, iv. a molded substance obtained by molding the bio-derived, bio-based or fermentation-derived polymer of ii. or the bio-derived, bio based or fermentation-derived resin of iii., or any combination thereof, v. a bio-derived, bio-based or fermentation-derived formulation comprising the bio-derived, bio based or fermentation-derived composition of i., bio-derived, bio-based or fermentation-derived compound of i., bioderived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semisolid or a non-semi-solid stream, comprising the bioderived, bio based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof Unless otherwise defined, all technical and scientific terms used herein have the same meaning as commonly understood by one of ordinary skill in the art to which this disclosure pertains. Although methods and materials similar or equivalent to those described herein can be used to practice the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the present disclosure are set forth in the accompanying drawings and the description below. Other features, objects, and advantages of the present disclosure will be apparent from the description and drawings, and from the claims. The word "comprising" in the claims may be replaced by "consisting essentially of" or with "consisting of," according to standard practice in patent law.

DESCRIPTION OF DRAWINGS

FIG. 3 tabulates the experimental results from an Akta® Purifier experiment programmed to mimic the cyclical continuous adsorption sequence as outlined in FIG. 1.

FIG. 4 tabulates the experimental results from an Akta® Purifier experiment programmed to mimic the cyclical continuous adsorption sequence as outlined in FIG. 2.

DETAILED DESCRIPTION

Figure 1A:
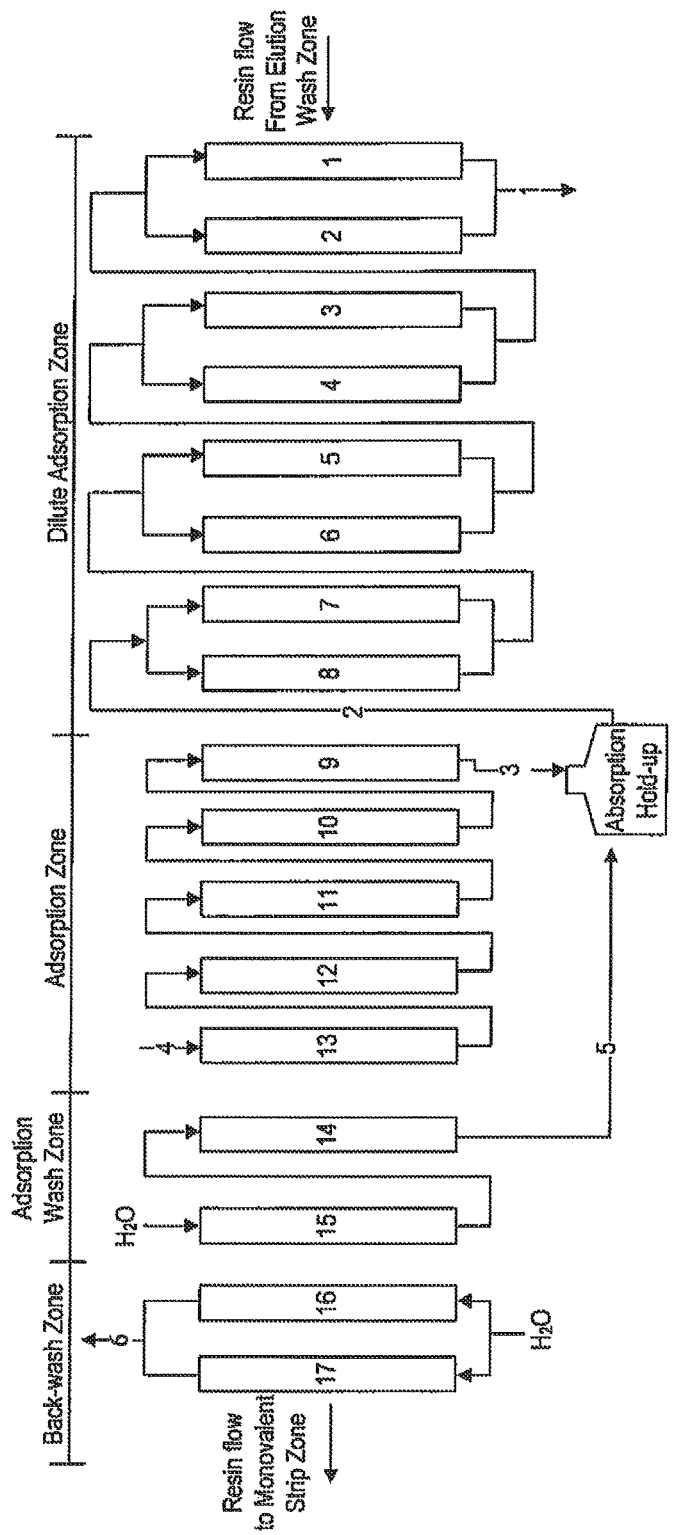
FIG. 1 is a schematic of an exemplary continuous ion exchange unit operation containing a separate Monovalent Strip Zone and a separate Monovalent Adsorption Zone, leading to the high purity and high concentration recovery of multivalent products prior to further purification.

Before the present embodiments are described, it is to be understood that the present disclosure is not limited to the particular apparatus, adsorbents, zones, methodologies or protocols described, as these may vary. It is also to be understood that the terminology used in the description is for the purpose of describing the particular versions or embodiments only, and is not intended to limit the scope of the present disclosure.

In general, this document provides, according to certain embodiments, for a continuous ion exchange unit operation, divided into a number of operating zones, producing a multivalent product for further purification. Such multivalent products include, but are not limited to; amino acids such as L-arginine; dicarboxylic acids such as, succinic acid, glutaric acid, adipic acid, pimelic acid and diamines such as putrescine, cadaverine, hexamethylenediamine and heptamethylenediamine, all of which are referred to as multivalent products herein. As used herein, the term "divalent" is used to denote a charged specie having either a 2+ or 2− valence. The term "monovalent" is used herein to denote a charged specie having either a 1+ or 1− valence. The term "first equivalence point" is used herein to denote the multivalent product's species distribution at $pH=0.5 \cdot (pK_{a1}+pK_{a2})$, where $pK_{a1}$ and $pK_{a2}$ are the first two acid dissociation constants for the multivalent product.

As used herein, the terms "unclarified" refers to a solution containing solid particulates such as cells or precipitates and "clarified" solutions are understood to mean a solution from which solid particulates have been removed.

As used herein, "adsorption zone" is understood to mean a stage in the recovery method comprising at least one column where the process stream containing the multivalent product to be recovered is added to a particular adsorbent resin and adsorbs to the adsorbent resin.

"Elution zone," as used herein, is understood to mean a stage in the recovery method where the multivalent product adsorbed to the adsorbent resin is desorbed into the liquid phase.

As used herein, "monovalent strip zone" is understood to mean a stage in the recovery method, where monovalent by-products are desorbed from the adsorbent and the valence of the multivalent product is changed from divalent to monovalent. The term "monovalent adsorption zone" is understood to mean a stage in the recovery method comprising at least one column where the majority of multivalent product absorbed is the monovalent specie.

The terms "about" and "approximately" when used in connection with a specific value, means that acceptable deviations from that value are also encompassed but still provide substantially the same function as the specific value.
Selective Adsorption and Particulate Removal A clarified or unclarified aqueous solution is pH adjusted to approximately the $pK_{a1}$ for cationic divalent products and to approximately the $pk_{a2}$ for anionic divalent products and fed to the Adsorption Zone (see e.g., STREAM 4, FIG. 1), fed counter-current to the flow of the adsorbent phase.

The flow-through from the Adsorption Zone (see e.g., STREAM 3, FIG. 1) is combined with the flow-through from the Adsorption Wash Zone (see e.g., STREAM 5, FIG. 1) into an adsorption hold-up vessel, subsequently fed to the Dilute Adsorption Zone (see STREAM 2, FIG. 1). The Adsorption Zone and Dilute Adsorption Zone facilitate adsorption of the multivalent product in principally the divalent state onto the adsorbent phase, competing for adsorption sites with other charged inorganic and organic species in the aqueous medium. The adsorbent flow rate is set to allows for minimal or zero break-through of the multivalent product into the adsorption effluent (see e.g., STREAM 1, FIG. 1), whilst allowing for flow through of inorganic and organic charged and uncharged/zero valence species to waste treatment.

The adsorbent and interstitial hold-up in the Adsorption Zone (see e.g., COL POS: 13, FIG. 1) moves into the Adsorption Wash Zone. Water fed into the Adsorption Wash Zone (see e.g., COL POS: 15, FIG. 1) flushes the interstitial hold-up from the Adsorption Zone into the adsorption hold-up vessel, ensuring that no multivalent product, held interstitially, is carried forward into the Back wash Zone.

Figure 1B:
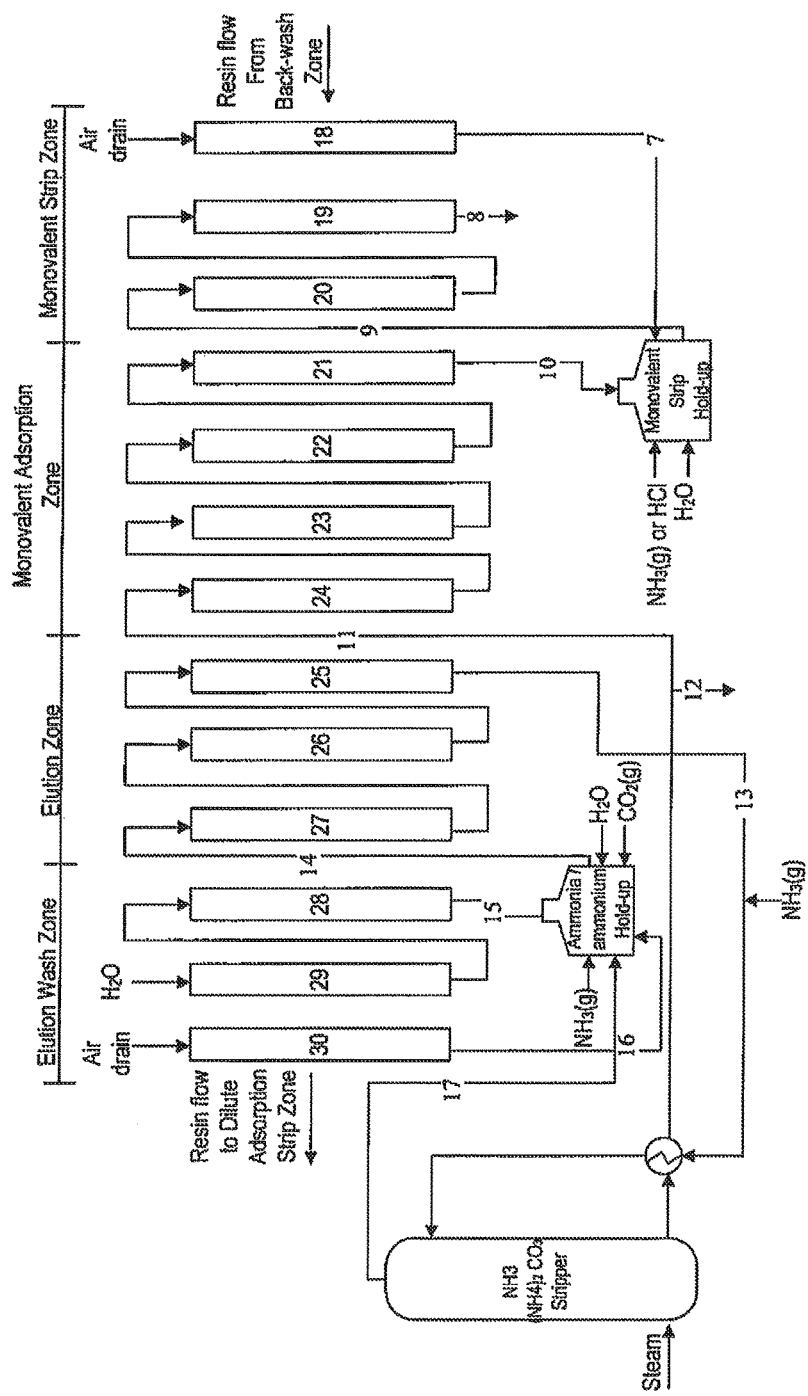

The Back-wash Zone fluidises the resin beds (see e.g., COL POS: 16 & 17), providing for entrained particulate removal from the resin beds (see e.g., STREAM 6, FIG. 1).

Increasing Purity and Concentration of Adsorbed Multivalent Product Using a Separate Monovalent Strip Zone and a Separate Monovalent Adsorption Zone The adsorbed multivalent product moves from the Back-wash Zone (see e.g., COL POS: 17, FIG. 1) into the Monovalent Strip Zone (cee e.g., COL POS: 18, FIG. 1). An air drain (see e.g., COL POS: 18, FIG. 1), recovers the interstitial water holdup carried forward from the Back-wash Zone into the monovalent strip hold-up vessel (see e.g., STREAM 7, FIG. 1).

The monovalent strip bold-up vessel is charged with a base such as $NH_3(g)$ or an acid such as HCl or $H_2SO_4$ at a concentration that allows for the effluent pH from the Monovalent Strip Zone (see e.g., STREAM 8, FIG. 1) to be approximately the $pK_{a2}$ for cationic divalent products and approximately the $pK_{a1}$ for anionic divalent products. The Monovalent Strip Zone is fed from the Monovalent strip hold-up vessel (see e.g., STREAM 9, FIG. 1), desorbing adsorbed species that are uncharged or having zero valence between the pH of the monovalent strip hold-up vessel and the first equivalence point. Consequently, the multivalent product is converted from the principally divalent to the largely monovalent state, freeing adsorption sites for use in the Monovalent Adsorption Zone. The flow through from the Monovalent Strip Zone is diverted to waste water treatment (see e.g. STREAM 8, FIG. 1).

Ammonia/ammonium carbonate steam stripping (see FIG. 1) to approximately the first equivalence point, produces a multivalent product that has a principally monovalent valence species distribution. The Monovalent Adsorption Zone is fed from the ammonia/ammonium carbonate stripper (see e.g., STREAM 11, FIG. 1), providing for adsorption of the monovalent specie of the multivalent product onto the free adsorbent sites, thereby increasing the concentration of the multivalent product adsorbed to the adsorbent phase. The Monovalent Adsorption Zone feed rate is set to allow for minimal or zero break-through of the multivalent product into the flow through (see e.g. STREAM 10, FIG. 1). The flow through (see e.g., STREAM 10, FIG. 1) from the Monovalent Adsorption Zone is recovered into the monovalent strip holdup vessel.

The adsorbed monovalent specie of the multivalent product moves from the Monovalent Adsorption Zone (see e.g., COL POS: 24, FIG. 1) into the Elution Zone (see COL POS: 25, FIG. 1). The Elution Zone is fed from a high concentration ammonia/ammonium hold-up vessel (see e.g., STREAM 14, FIG. 1), eluting all multivalent product from the adsorbent. The eluate (see e.g., STREAM 13, FIG. 1) is fed to the ammonia/ammonium carbonate stripper, recovering free ammonia and carbon dioxide as feed to the concentration ammonia/ammonium hold-up vessel (see e.g., STREAM 17, FIG. 1).

The regenerated resin moves from the Elution Zone (see e.g., COL POS: 27, FIG. 1) into the Elution Wash Zone (see e.g., COL POS: 28, FIG. 1). An aqueous solution, for example, water, is fed into the Elution Wash Zone (see e.g., COL POS: 29, FIG. 1) and flushes interstitial ammonia/ammonium (bi)carbonate into the concentrated ammonia/ammonium hold-up vessel (See e.g. STREAM 15, FIG. 1). Finally, the interstitial water is recovered via an air drain (see e.g., COL POS: 30, FIG. 1) into the concentrated ammonia/ammonium hold-up (see e.g., STREAM 16, FIG. 1).

The adsorbent moves from the Elution Wash Zone (see e.g., COL POS: 30, FIG. 1) into the Dilute Adsorption Zone (see e.g., COL POS: 1, FIG. 1) and the adsorbent repeats the passage through the various carousel zones as described above.

STREAM 12 (see FIG. 1) represents the net flow of multivalent product to further down-stream processing.

Figure 2A:
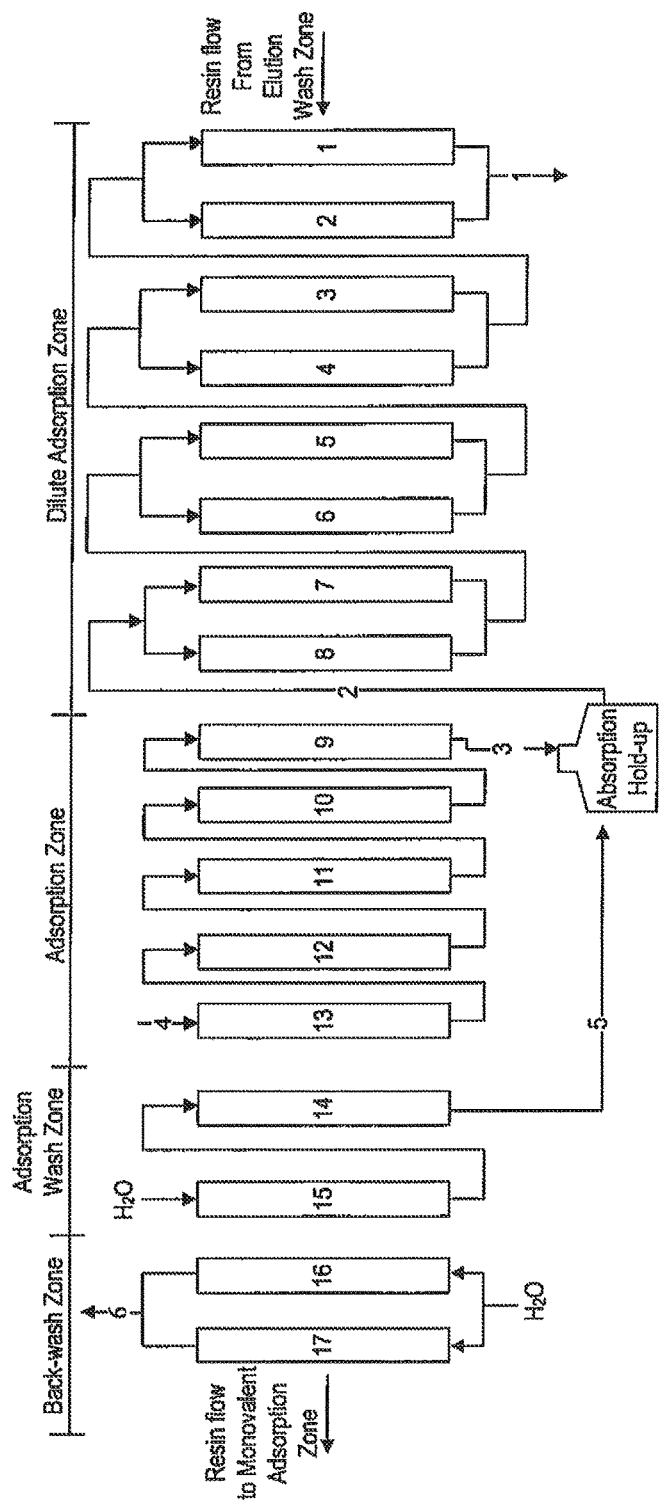
FIG. 2 is a schematic of an exemplary continuous ion exchange unit operation containing a combined Monovalent Strip Zone and a Monovalent Adsorption Zone, leading to the high purity and high concentration recovery of multivalent products prior to further purification.
Figure 2B:
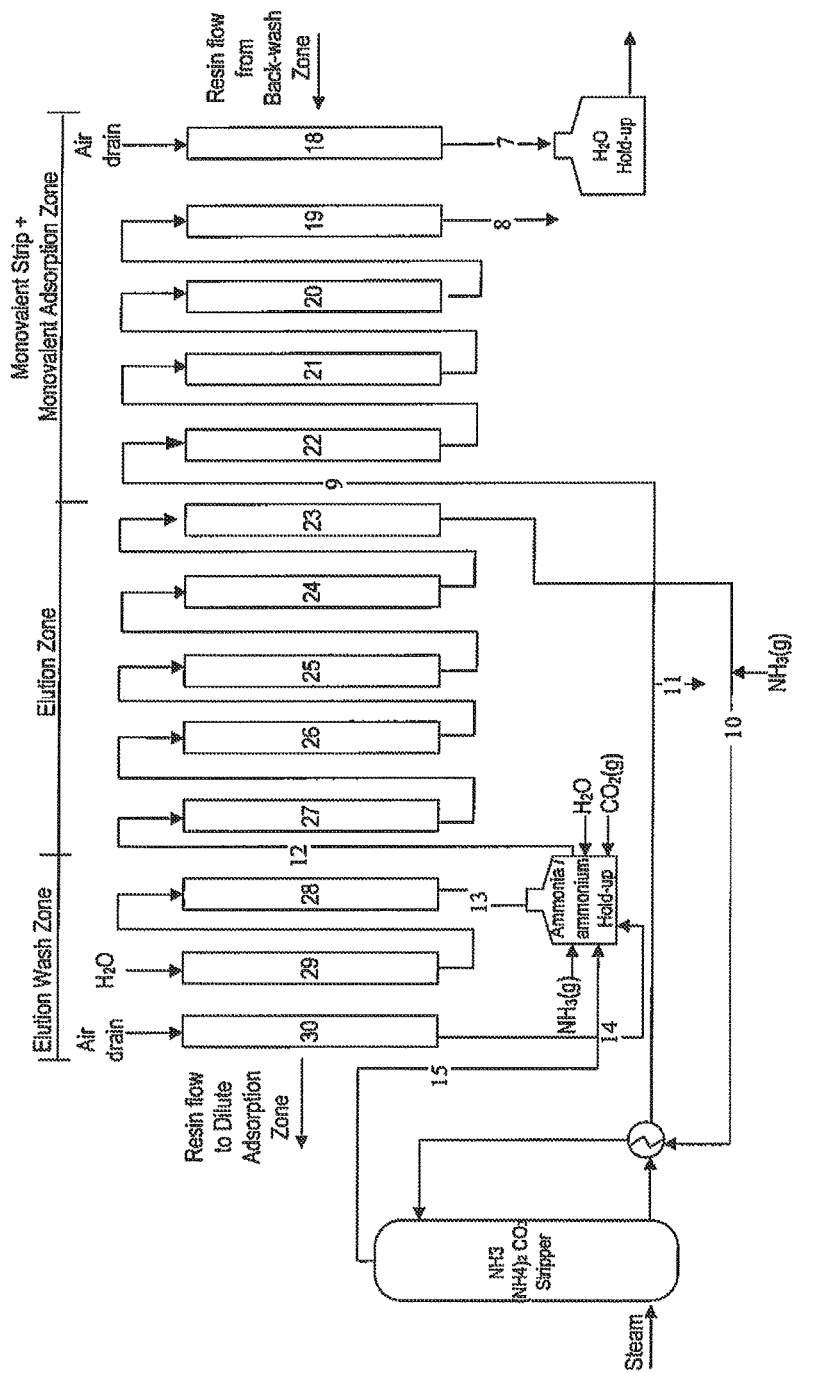

Increasing Purity and Concentration of adsorbed Multivalent Product Using a Combined Monovalent Strip Zone and Monovalent Adsorption Zone The adsorbed multivalent product moves from the Back-wash Zone (see e.g., COL POS: 17, FIG. 2) into the combined Monovalent Strip and Adsorption Zone (see e.g. COL POS: 18, FIG. 2). An air drain (see e.g., COL POS: 18, FIG. 2), recovers the interstitial water hold-up carried forward from the Back-wash Zone into a water recovery hold-up vessel (see e.g., STREAM 7, FIG. 2).

Ammonia/ammonium carbonate steam stripping (see FIG. 2) to a pH where the multivalent product has a principally zero valence species distribution is fed to the combined Monovalent Strip and Adsorption Zone (see e.g., STREAM 9, FIG. 2), desorbing adsorbed species that are uncharged or having zero valence between the feed (see e.g., STREAM 9, FIG. 2) and effluent pH (see e.g., STREAM 8, FIG. 2). Consequently, the multivalent product adsorbed to the adsorbent is converted from the principally divalent to the largely monovalent state, freeing adsorption sites. Also, the zero valence multivalent product in the feed (see e.g., STREAM 9, FIG. 2) is converted to the monovalent state and adsorbed onto the free adsorbent sites, thereby increasing the concentration of the multivalent product adsorbed to the adsorbent phase. The combined Monovalent Strip and Adsorption Zone feed rate is set to allow for minimal or zero break-through of the multivalent product into the flow through (see e.g., STREAM 8, FIG. 2). The flow through (see e.g., STREAM 8, FIG. 2) from the Monovalent Adsorption Zone is diverted to waste water treatment.

The adsorbed monovalent specie of the multivalent product moves from the combined Monovalent Strip and Adsorption Zone (see e.g., COL POS: 22, FIG. 2) into the Elution Zone (see e.g., COL POS: 23, FIG. 2). The Elution Zone is fed from a high concentration ammonia/ammonium hold-up vessel (see e.g., STREAM 12, FIG. 2), eluting all multivalent product from the adsorbent. The eluate (see e.g., STREAM 10, FIG. 2) is fed to the ammonia ammonium carbonate stripper, recovering free ammonia and carbon dioxide as feed to the concentration ammonia/ammonium hold-up vessel (see e.g., STREAM 15, FIG. 2).

The regenerated resin moves from the Elution Zone (see e.g., COL POS: 27, FIG. 2) into the Elution Wash Zone (see e.g., COL POS: 28, FIG. 2). An aqueous solution, for example, water, is fed into the Elution Wash Zone (see e.g., COL POS: 29, FIG. 2) and flushes interstitial ammonia/ammonium (bi)carbonate into the concentrated ammonia ammonium hold-up vessel (see e.g. STREAM 13, FIG. 2). Finally, the interstitial water is recovered via an air drain (see e.g., COL POS: 30, FIG. 2) into the concentrated ammonia/ammonium hold-up (see e.g., STREAM 14, FIG. 2).

The adsorbent moves from the Elution Wash Zone (see e.g., COL POS: 30, FIG. 2) into the Dilute Adsorption Zone (see e.g., COL. POS: 1, FIG. 2) and the adsorbent repeats the passage through the various carousel zones as described above. STREAM 11 (see FIG. 1) represents the net flow of multivalent product to further down-stream processing.

EXAMPLES

Example 1

Recovery of Hexamethylenediamine from a Synthetic Feed Representing Clarified Fermentation Broth Using Continuous Ion Exchange with Separate Monovalent Strip and Separate Monovalent Adsorption Zone A column with a diameter of 25.4 [mm] was packed to a flee settled bed height of approximately 600 [mm] using virgin Dowex Monosphere 650C cationic exchange resin. The virgin resin was washed with purified water to remove solvents associated with its manufacture and converted to the $NH_4^+$ form using 10 [%] (w/w) $NH_3$(aq) and stored in purified water.

An Akta® Purifier was programmed to mimic the cyclical continuous adsorption sequence as contained in FIG. 1 for the purification of hexamethylenediamine (HMD) from a synthetic feed representing clarified fermentation broth. Accordingly, a synthetic solution having the feed purity as outlined in FIG. 3 was prepared as feed to the simulated. Adsorption Zone, having an HMD concentration of approximately 35 [g/L]. The feed to the simulated Adsorption Wash Zone was comprised of purified water. The simulated Monovalent Strip Zone feed comprised a 1 [%] (w/w) $NH_3$(aq) solution. The feed from the ammonia/ammonium carbonate stripper to the simulated Monovalent Adsorption Zone comprised a HMD solution buffered with ammonium bicarbonate to pH=10.5 [-], having a final concentration of approximately 35 [g/L]. The simulated Elution Zone feed contained 2 [M] ammonium carbonate. The simulated Elution Wash Zone feed was comprised of purified water. Each Zone was fed with 3 bed volumes at a constant flow rate of 5 [mL/min].

FIG. 3 tabulates the results from the simulated cyclical continuous adsorption experiment. FIG. 3 demonstrates that the purity of the HMD was increased from 77.4 [%] (w/w) in the feed to 99.2 [%] (w/w) in the eluate, the sequence having effectively rejected the four feed impurities down to trace quantities of lysine and glutamate. Also, the Monovalent Adsorption Zone concentrated the HMD product by a factor of 1.36. The results in FIG. 3 demonstrate that the continuous adsorption sequence outlined in FIG. 1 both purities and concentrates the desired product.

Example 2

Recovery of Hexamethylenediamine from a Synthetic Feed Representing Clarified Fermentation Broth Using Continuous Ion Exchange with a Combined Monovalent Strip and Monovalent Adsorption Zone A column with a diameter of 25.4 [mm] was packed to a free settled bed height of approximately 600 [mm] using virgin Dowex Monosphere 650C cationic exchange resin. The virgin resin was washed with purified water to remove solvents associated with its manufacture and converted to the $NH_4^+$ form using 10 [%] (w/w) $NH_3$(aq) and stored in purified water.

An Akta® Purifier was programmed to mimic the cyclical continuous adsorption sequence as contained in FIG. 2 for the purification of hexamethylenediamine (HMD) from a synthetic feed representing clarified fermentation broth. Accordingly, a synthetic solution having the feed purity as outlined in FIG. 4 was prepared as feed to the simulated Adsorption Zone, having an HMD concentration of approximately 54 [g/L]. The feed to the simulated Adsorption Wash Zone was comprised of purified water. The simulated combined Monovalent Strip and Adsorption Zone feed comprised a HMD solution in water, having a final concentration of approximately 54 [g/L]. The simulated Elution Zone feed contained 2 [M] ammonium carbonate. The simulated Elution Wash Zone feed was comprised of purified water. Each Zone was fed with 3 bed volumes at a constant flow rate of 5 [mL/min], barring the combined Monovalent Strip and Adsorption Zone which was fed with 2 bed volumes at a constant flow rate of 5 [mL/min].

FIG. 4 tabulates the results from the simulated cyclical continuous adsorption experiment. FIG. 4 demonstrates that the purity of the HMD was increased from 86 [%] (w/w) in the feed to 99.6 [%](w/w) in the eluate, the sequence having effectively rejected the four feed impurities down to trace quantities of lysine. Also, the combined Monovalent Strip and Adsorption Zone concentrated the HMD product by a factor of 1.38. The results in FIG. 4 demonstrate that the continuous adsorption sequence outlined in FIG. 2 both purifies and concentrates the desired product.

What is claimed is:

1. An apparatus for recovering one or more diamines from aqueous solutions comprising one or more of the below zones:
   (a) an adsorption zone comprising an ion exchange resin, for adsorption of the one or more diamines as a divalent species;
   (b) a monovalent strip zone, for desorbing impurities and converting the adsorbed one or more diamines to the monovalent state;
   (c) a monovalent adsorption zone, for adsorbing recycled diamines recycled from a steam stripper; and
   (d) an elution zone, for eluting the one or more diamines using a concentrated ammonia, ammonium bicarbonate or ammonium carbonate solution.

2. The apparatus according claim 1, wherein the one or more diamines are chosen from putrescine, cadaverine, hexamethylenediamine, and heptamethylenediamine.

3. The apparatus of claim 1, which is configured to selectively desorb impurities and (2) to convert the adsorbed one or more diamines to principally the monovalent state by feeding a base or an acid at a concentration that allows the pH of the aqueous solution discharged from the resin to be approximately the $pK_{a2}$ for cationic divalent products and to be approximately the $pK_{a1}$ for anionic divalent products.

4. The apparatus of claim 3, wherein multivalent product at a pH of approximately the first equivalence point is recycled to the ion exchange resin and concentrated through re-adsorption.

5. The apparatus of claim 1, wherein (1) impurities are selectively desorbed and (2) the adsorbed one or more diamines are converted to principally the monovalent state by recycling the one or more diamines in principally the zero valence state, concentrating the one or more diamines though re-adsorption.

6. The apparatus of claim 1, wherein the one or more diamines are eluted from the ion exchange resin with a high concentration of ammonia, ammonium bicarbonate and/or ammonium carbonate.

7. The apparatus of claim 6, where the eluted one or more diamines are fed to a steam stripper, adjusting the pH of the one or more diamines to approximately the first equivalence point.

8. The apparatus of claim 6, where the eluted one or more diamines are fed to a steam stripper, adjusting the pH to where the one or more diamines are principally in the zero valence state.

9. The apparatus of claim 7, where a fraction of the one or more diamines recovered from the steam stripper is recycled to the ion exchange resin and concentrated through re-adsorption.

10. The apparatus of claim 1, further comprising at least one elution wash zone after one or more of zones (a), (b), (c), and (d) using an aqueous solution.

11. The apparatus of claim 1, wherein the monovalent strip zone and the monovalent adsorption zone are combined.

12. The apparatus of claim 8, where a fraction of the one or more diamines recovered from the steam stripper is recycled to the ion exchange resin and concentrated through re-adsorption.

* * * * *